United States Patent [19]

Baus et al.

[11] Patent Number: 4,945,166
[45] Date of Patent: Jul. 31, 1990

[54] PREPARATION OF N-HYDROXYPYRAZOLES

[75] Inventors: Ulf Baus, Dossenheim; Wolfgang Reuther, Heidelberg; Rolf Fikentscher, Ludwigshafen, all of Fed. Rep. of Germany

[73] Assignee: BASF Aktiengesellschaft, Ludwigshafen, Fed. Rep. of Germany

[21] Appl. No.: 367,053

[22] Filed: Jun. 16, 1989

[30] Foreign Application Priority Data

Jun. 18, 1988 [DE] Fed. Rep. of Germany ....... 3820738

[51] Int. Cl.$^5$ .................. C07D 231/12; C07D 231/54; C07D 231/56
[52] U.S. Cl. .................... 548/369; 548/371; 548/372; 548/375; 548/376
[58] Field of Search ............... 548/369, 371, 372, 375, 548/376

[56] References Cited

U.S. PATENT DOCUMENTS 4,350,819  9/1982  Rieber et al. .......... 548/375

OTHER PUBLICATIONS

Freeman et al., J. Org. Chem., vol. 34, (1969), pp. 187–194.

*Primary Examiner*—Robert W. Ramsuer
*Attorney, Agent, or Firm*—Oblon, Spivak, McClelland, Maier & Neustadt

[57] ABSTRACT

N-hydroxypyrazoles of the general formula I

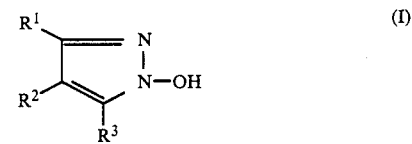

where $R^1$, $R^2$ and $R^3$ may be identical or different and are each hydrogen, alkyl, halogen or aryl, or $R^1$ and $R^2$ or $R^2$ and $R^3$ together with the carbon atoms carrying these radicals form an aromatic or nonaromatic ring of 5 or 6 carbon atoms are prepared by a process in which (A) a pyrazole of the general formula II

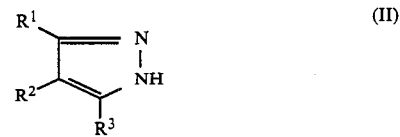

is converted in a conventional manner with an alkali metal hydroxide, alkali metal hydride or alkali metal carbonate into one of its metal salts of the general formula III

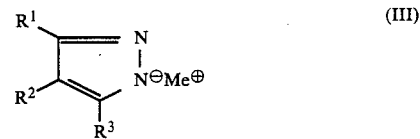

where ME⊕ is a cation of an alkali metal, and
(B) the resulting metal salt of the general formula III is reacted with dibenzoyl peroxide in an inert organic solvent or in a 2-phase system, in the presence or absence of a phase transfer catalyst.

8 Claims, No Drawings

PREPARATION OF N-HYDROXYPYRAZOLES

The present invention relates to the preparation of N-hydroxypyrazole and its derivatives from the corresponding pyrazoles.

N-Hydroxypyrazole and its derivatives are important intermediates for the preparation of substances having a broad biological action spectrum. For example, DE No. 3 409 317 describes the preparation of useful nitrification inhibitors for ammonium nitrogen from N-hydroxypyrazoles. Furthermore, DE No. 35 32 880 describes the preparation of 1,4-disubstituted derivatives of N-hydroxypyrazole as compounds having a selective action on histamine $H_2$ receptors. There has therefore been no lack of attempts to find an advantageous process for the preparation of N-hydroxypyrazoles.

According to German Laid-Open Application DOS No. 3,031,385, N-hydroxypyrazole is prepared by a multistage synthesis from the building blocks azodicarboxylate, cyclopentadiene, nitrile oxide and a peroxide. The disadvantages of this process are the multistage reaction, the low yield and the fact that the N-hydroxypyrazole is obtained as a mixture with isoxazoles.

N-Hydroxypyrazoles substituted in the nucleus can be prepared, for example as described in J. Org. Chem. 34 (1969), 187–194, by nitrosation of appropriately substituted $\alpha,\beta$-unsaturated oximes followed by reduction of the 3,4-diazacyclopentadienone dioxides obtained. The disadvantages of this process are the multistage procedure and the fact that only N-hydroxypyrazoles substituted in the nucleus can be prepared.

It is an object of the present invention to provide a simple and economical process which permits the preparation of both N-hydroxypyrazole itself and N-hydroxypyrazoles substituted in the nucleus.

We have found that this object is achieved and that, surprisingly, N-hydroxypyrazole itself and N-hydroxypyrazoles substituted in the nucleus are obtained in a simple manner if the corresponding pyrazoles are converted into their alkali metal salts and the latter are reacted with a diacyl peroxide, preferably with dibenzoyl peroxide, under defined reaction conditions.

Although it was known that hydroxylamines can be prepared by reacting primary or secondary aliphatic amines with hydrogen peroxide or its acyl derivatives, such as dibenzoyl peroxide, in combination with catalysts and then hydrolyzing the resulting O-benzoyl-N-hydroxylamines (cf. Houben-Weyl, Methoden der organischen Chemie, Vol. 10/1, Thieme-Verlag, 1971, pages 1135–1137), this reaction is expressly restricted to aliphatic amines (loc. cit.).

The present invention accordingly relates to a process for the preparation of N-hydroxypyrazoles of the general formula I

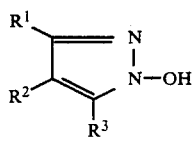

where $R^1$, $R^2$ and $R^3$ may be identical or different and are each hydrogen, alkyl, cycloalkyl, aryl or halogen, or $R^1$ and $R^2$ or $R^2$ and $R^3$ together with the carbon atoms carrying these radicals form an aromatic or nonaromatic ring of 5 or 6 carbon atoms, wherein (A) a pyrazole of the general formula II

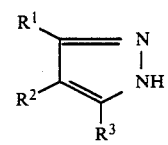

where $R^1$, $R^2$ and $R^3$ have the meanings stated for formula I, is converted in a conventional manner with an alkali metal hydroxide, alkali metal hydride or alkali metal carbonate into one of its metal salts of the general formula III

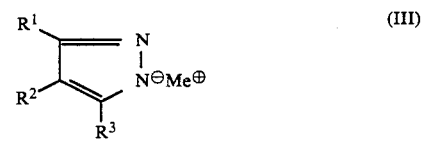

where $R^1$, $R^2$ and $R^3$ have the meanings stated for formula I and $Me^\oplus$ is a cation of an alkali metal, and (B) the resulting metal salt of the general formula III is reacted with a diacyl peroxide, preferably dibenzoyl peroxide.

Examples of suitable pyrazoles of the general formula II are indazole, 3-phenylpyrazole, 4-phenylpyrazole, 3,5-diphenylpyrazole, 3,4,5-triphenylpyrazole, 3,5-diphenyl-4-methylpyrazole, 4,5-dimethylpyrazole and 3,4,5-trimethylpyrazole.

Preferred pyrazoles of the formula II are, for example, pyrazole itself, 4-chloropyrazole, 4-bromopyrazole, 4-iodopyrazole and 3,5-dimethylpyrazole.

The pyrazoles are converted into their metal salts of the general formula III in a conventional manner by reacting the pyrazole in an inert solvent with an alkali metal hydroxide, alkali metal hydride or alkali metal carbonate at from 0° to 50° C.

Suitable diacyl peroxides are symmetric aliphatic or aromatic diacyl peroxides. Examples are dilauryl peroxide, didecanoyl peroxide, bis-(3,5,5-trimethylhexanoyl) peroxide, bis-(3-chlorobenzoyl) peroxide and bis-(2,4-dichlorobenzoyl) peroxide. The symmetric diacyl peroxides can be prepared in a simple manner by reacting $H_2O_2$ with an acyl chloride in the presence of an alkali metal hydroxide or alkali metal carbonate. However, asymmetric diacyl peroxides, for example phenyl acetyl peroxide, can also be used for the novel reaction. They are obtained by reacting a percarboxylic acid with an acyl chloride in the presence of an alkali metal hydroxide or carbonate. Dibenzoyl peroxide is particularly advantageously used.

The novel process can be carried out advantageously in various ways. In one possible method, the pyrazole of the formula II in an inert organic solvent is converted in a conventional manner into one of its metal salts of the formula III, after which a solution of very dry dibenzoyl peroxide in an inert solvent is added to the resulting solution or suspension of the metal salt of the formula III in such a way that the reaction temperature is from 0° to 60° C., preferably from 5° to 20° C.

The dibenzoyl peroxide required for this reaction can be prepared in a simple manner by reacting $H_2O_2$ with benzoyl chloride in the presence of an alkali metal hydroxide or alkali metal carbonate.

It can be used in a dry or moist state; the best yields are obtained if a solution of dried dibenzoyl peroxide is used.

Suitable solvents for this reaction are aliphatic ethers, such as diethyl ether, diisopropyl ether or diethylene glycol dimethyl ether; aliphatic hydrocarbons, such as pentane, hexane or cyclohexane; cyclic ethers, such as tetrahydrofuran (THF) or dioxane, and aromatic hydrocarbons, such as benzene or toluene.

Diethyl ether, THF and toluene are particularly advantageously used.

The stoichiometric ratio of III to dibenzoyl peroxide may vary from 1 : 1 to 5 : 1; preferably, an excess of the pyrazole salt III is used, i.e. about a ratio of from 2 : 1 to 3 : 1.

In general, the reaction is complete after the end of the addition. In some cases, however, it is advantageous to continue stirring the reaction mixture for a short time at room temperature.

However, it is not absolutely essential to employ completely dry dibenzoyl peroxide. Very small amounts of moisture or the presence of about 1 equivalent of water per equivalent of pyrazole, as formed in the preparation of the metal salts of the formula III from the pyrazole and the alkali metal hydroxide, reduce the yields of hydroxypyrazoles by only an insignificant extent.

It may however also be very advantageous to employ a relatively large amount of water if the reaction is carried out in a solvent which is water-immiscible or only slightly miscible with water, and catalytic amounts of a phase transfer catalyst, for example a quaternary ammonium salt, are added to the reaction mixture.

The present invention therefore relates to a process for the preparation of N-hydroxypyrazoles of the general formula I, wherein (A) a pyrazole of the general formula II in water is converted in a conventional manner with an alkali metal hydroxide or alkali metal carbonate into a solution or suspension of one of its metal salts of the general formula III and (B) the resulting metal salt of the general formula III or its solution or suspension in water is reacted with dibenzoyl peroxide in the presence of a suitable phase transfer catalyst in a 2-phase system consisting of water and an inert organic solvent which is water-immiscible or only slightly miscible with water.

This variant of the novel process has the great advantage that it is possible to use the commercial solid dibenzoyl peroxide desensitized with a relatively large amount of water (in general 25% of water), with the result that special safety measures which are essential when working with solutions of substantially dry dibenzoyl peroxide can be dispensed with.

The novel process can be carried out using a large number of phase transfer catalysts (for a general overview, see V. Dehmlow, Angew. Chem. 89 (1977), 521–533). Particularly preferred phase transfer catalysts are:

1. tetraalkylammonium salts of the general formula IV

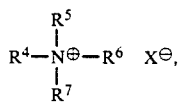

where $R^4$, $R^5$, $R^6$ and $R^7$ may be identical or different and are each alkyl of 1 to 22 carbon atoms or alkyl of not more than 25 carbon atoms which contains functional groups such as hydroxyl, carboxamide or ether groups, e.g. methyl, ethyl, (iso)propyl, butyl, octyl, dodecyl, $C_{16}H_{33}$, hydroxy(iso)propyl or

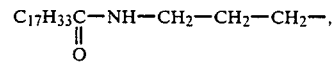

or phenyl or phenyl-substituted alkyl (e.g. benzyl) of not more than 20 carbon atoms, and $X^\ominus$ is an anion of an acid, such as $I^-$, $Cl^-$, $Br^-$, $(HSO_4)^-$, $(CN)^-$, $(BF_4)^-$ or $OH^-$, in particular the very economical trimethylbenzylammonium chloride, which can be used in the form of its 50% strength aqueous solution, and tricaprylmethylammonium chloride; and 2. tetraalkylphosphonium salts of the general formula V

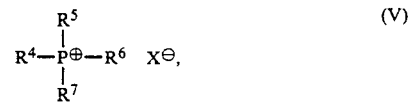

where $R^4$, $R^5$, $R^6$, $R^7$ and $X^\ominus$ may have the meanings stated for formula (IV), in particular tri-n-octylmethylphosphonium iodide.

Mixtures of the abovementioned phase transfer catalysts and supported phase transfer catalysts are also suitable.

The phase transfer catalysts are used for the novel process in amounts of from 0.1 to 1, preferably from 0.3 to 0.5, mole per mole of pyrazole.

The stoichiometric ratio of the metal salt III to dibenzoyl peroxide is advantageously chosen somewhat higher for this variant. It may vary from 1 : 1 to 10 : 1, preferably from 3 : 1 to 6 : 1.

The following procedures for the novel process have proven particularly useful:

(1) Commercial dibenzoyl peroxide in the solid state, desensitized with a relatively large amount of water, is added at room temperature to a 2-phase system which has been prepared from water, an alkali metal hydroxide, a pyrazole of the formula II, a phase transfer catalyst and an inert solvent which is water-immiscible or only slightly miscible with water.

(2) Commercial dibenzoyl peroxide in a 2-phase system consisting of water, a pyrazole of the formula II, a phase transfer catalyst and an inert organic solvent which is water-immiscible or only slightly miscible with water is initially taken and the reaction is initiated by adding an alkali metal hydroxide.

In the first procedure, however, the dibenzoyl peroxide to be used can also be dissolved in a solvent and the solution metered into the 2-phase system, if necessary after removing water which has separated out.

The alkali metal hydroxide used is in general KOH or NaOH. It can be used in powder form or as an aqueous solution. It is used in general in amounts of from 1 to 10, preferably from 1 to 1.5, moles per mole of pyrazole.

The water may be present in the reaction mixture in amounts of from 1 to >100 moles per mole of pyrazole. Examples of solvents which are water-immiscible or only slightly miscible with water are aromatic hydrocarbons, such as benzene or toluene, halohydrocarbons, such as methylene chloride, chloroform or chlorobenzene, and aliphatic hydrocarbons, such as cyclohexane.

To work up the reaction mixture, water is generally added to it, the mixture is mixed thoroughly and the aqueous phase is separated off. The benzoic acid formed in the reaction can then be precipitated, for example by acidifying the aqueous phase with an acid, such as sulfuric acid, and can be extracted or separated off by filtration.

Thereafter, the desired N-hydroxypyrazole and excess pyrazole can be transferred to the organic phase by extraction at weakly acidic pH with a suitable solvent, for example ethyl acetate, and can be isolated by distillation after the solvent has been distilled off. For this purpose, the mixture is rendered weakly basic and evaporated down in a rotary evaporator under greatly reduced pressure (>7 mbar). The solid residue is slightly acidified and extracted with, for example, ethyl acetate. The ethyl acetate phase is dried and evaporated down. The remaining residue can be recrystallized from cyclohexane. In this way, the pyrazole used in excess and not consumed is recovered, and very pure N-hydroxypyrazole is obtained.

With the aid of the novel process, the N-hydroxypyrazoles which are desirable intermediates for a large number of active ingredients can be obtained in a very simple and economical manner in good yields and in pure form.

The Examples which follow illustrate the novel process.

EXAMPLE 1

(a) 20.4 g (0.3 mole) of pyrazole were dissolved in 500 ml of tetrahydrofuran (THF) and 9 g (0.3 mole) of an 80% strength by weight suspension of NaH in liquid paraffin were added a little at a time at room temperature (RT). After evolution of hydrogen was complete, the mixture was cooled to 5° C. and 24.2 g (0.1 mole) of dry dibenzoyl peroxide, dissolved in 500 ml of THF, were added at a rate such that the temperature of the reaction mixture did not exceed 25° C.

After the addition was complete, stirring was carried out for a further 10 minutes (min) and the reaction mixture was mixed with ice water and petroleum ether (bp.=30°-60° C.) and shaken. The aqueous phase was separated off and acidified by adding sulfuric acid. After repeated extraction with cyclohexane, the aqueous phase was brought- to pH 8 by adding KOH solution and then evaporated down under greatly reduced pressure (<7 mbar/water bath>30° C.). The precipitated salt was taken up in a little water and the solution was slightly acidified with sulfuric acid and extracted by shaking with ethyl acetate. The organic phase was dried with sodium sulfate and the solvent was removed in a rotary evaporator.

Yield: 3.95 g (corresponding to 47% of theory, based on converted pyrazole); melting point: 74° C. (literature melting point: 74° C.).

The following N-hydroxypyrazoles were prepared from correspondingly substituted pyrazoles in a similar manner:

| Hydroxypyrazole | Yield [% of theory] | Melting point [°C.] |
| --- | --- | --- |
| (b) 4-Chloro-N-hydroxypyrazole | 58 | 122 |
| (c) 4-Iodo-N-hydroxypyrazole | 27 | 125 |
| (d) 3,5-dimethyl-N-hydroxy-pyrazole | 25 | 155 |

EXAMPLE 2

(a) 27.2 g (0.4 mole) of pyrazole were dissolved in 300 ml of toluene. 25.4 g (0.43 mole) of KOH powder (88% strength) were added to the stirred solution and the mixture was cooled to 20° C. 0.3 g (0.013 mole) of benzyl triethylammonium chloride was added, after which 24.5 g (0.075 mole) of dibenzoyl peroxide (stabilized with 25% of water) were introduced a little at a time, the temperature in the reaction flask being kept at 20° C. When the addition was complete, stirring was continued for a further 2 hours, after which 100 ml of water were added and the phases were separated. The aqueous phase was acidified with sulfuric acid and the precipitated benzoic acid was filtered off. The filtrate was extracted with 3 times 100 ml of ethyl acetate at weakly acidic pH and the combined organic phases were dried with sodium sulfate. The solvent was then removed in a rotary evaporator.

The remaining oily crude product was worked up similarly to Example 1.

Yield: 4.2 g (corresponding to 75% of theory, based on converted pyrazole).

The following N-hydroxypyrazoles were prepared from correspondingly substituted pyrazoles in a similar manner:

| Hydroxypyrazole | Yield [% of theory] | Melting point [°C.] |
| --- | --- | --- |
| (b) 4-Chloro-N-hydroxypyrazole | 65 | 122 |
| (c) 4-Iodo-N-hydroxpyrazole | 20 | 125 |

We claim:

1. A process for the preparation of an N-hydroxypyrazole of the formula I

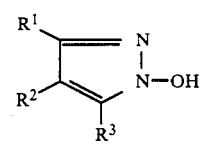

(I)

where $R^1$, $R^2$ and $R^3$ may be identical or different and are each hydrogen, alkyl, halogen or aryl, or $R^1$ and $R^2$ or $R^2$ and $R^3$ together with the carbon atoms carrying these radicals form an aromatic or nonaromatic ring of 5 or 6 carbon atoms, wherein (A) a pyrazole of the formula II

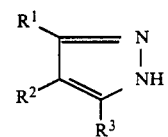

(II)

where $R^1$, $R^2$ and $R^3$ have the meanings stated for formula I, is converted in a conventional manner with an alkali metal hydroxide, alkali metal hydride or alkali metal carbonate into one of its metal salts of the formula III

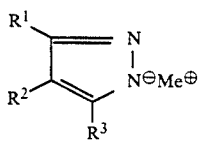

where $R^1$, $R^2$ and $R^3$ have the meanings stated for formula I and $Me^{\oplus}$ is a cation of an alkali metal, and (B) the resulting metal salt of the formula III is reacted with a diacyl peroxide.

2. A process as claimed in claim 1, wherein the diacyl peroxide used is dibenzoyl peroxide.

3. A process as claimed in claim 2, wherein
(A) a pyrazole of the formula II in an inert solvent is converted into one of its metal salts of the formula III and
(B) a solution of dry dibenzoyl peroxide in an inert solvent is added to the resulting solution or suspension of the metal salt of the formula III in such a way that the reaction temperature is from 0° to 60° C.

4. A process as claimed in claim 2, wherein the metal salt of the formula III is reacted with the dibenzoyl peroxide in the presence of a roughly equimolar amount of water.

5. A process as claimed in claim 2, wherein
(A) a pyrazole of the formula II in water is converted in a conventional manner with an alkali metal hydroxide or alkali metal carbonate into a solution or suspension of one of its metal salts of the formula III and
(B) the resulting metal salt of the formula III or its solution or suspension in water is reacted with dibenzoyl peroxide in the presence of a suitable phase transfer catalyst in a 2-phase system consisting of water and an inert organic solvent which is water-immiscible or only slightly miscible with water.

6. A process as claimed in claim 5, wherein the phase transfer catalyst used is a quaternary ammonium salt or hydroxide.

7. A process as claimed in claim 5, wherein commercial dibenzoyl peroxide in the solid state, desensitized with a relatively large amount of water, is added at room temperature to a 2-phase system prepared from water, an alkali metal hydroxide, a pyrazole of the formula II, a phase transfer catalyst and an inert organic solvent which is water-immiscible or only slightly miscible with water.

8. A process as claimed in claim 5, wherein commercial dibenzoyl peroxide in a 2-phase system consisting of water, a pyrazole of the formula II, a phase transfer catalyst and an inert organic solvent which is water-immiscible or only slightly miscible with water is initially taken and the reaction is initiated by adding an alkali metal hydroxide.

* * * * *